United States Patent [19]

Bledsoe, Jr. et al.

[11] 4,249,028

[45] Feb. 3, 1981

[54] SELECTIVE CONVERSION OF D-ISOLIMONENE TO D-3-MENTHENE

[75] Inventors: James O. Bledsoe, Jr.; Carlos G. Cardenas, both of Jacksonville, Fla.

[73] Assignee: SCM Corporation, New York, N.Y.

[21] Appl. No.: 102,530

[22] Filed: Dec. 11, 1979

Related U.S. Application Data

[63] Continuation-in-part of Ser. No. 5,138, Jan. 22, 1979, Pat. No. 4,204,080.

[51] Int. Cl.³ .................. C07C 13/20; C07C 5/05; C07C 5/13; B01J 23/44
[52] U.S. Cl. ................................. 585/273; 585/355; 585/947
[58] Field of Search ............... 585/355, 273, 947, 350

[56] References Cited

U.S. PATENT DOCUMENTS

| | | | |
|---|---|---|---|
| 3,407,241 | 10/1968 | Booth | 585/947 X |
| 3,804,914 | 4/1974 | Fahey | 585/273 |
| 3,925,494 | 5/1975 | Fahey | 585/273 |
| 4,190,612 | 2/1980 | Masilamani et al. | 585/947 X |

*Primary Examiner*—Delbert E. Gantz
*Assistant Examiner*—G. E. Schmitkons
*Attorney, Agent, or Firm*—A. J. Gibbons

[57] ABSTRACT d-3-Menthene of high optical purity is obtained by the selective isomerization/hydrogenation of d-isolimonene in the presence of minor amounts of a palladium catalyst at temperatures up to 200° C. and pressures of preferably about 100–500 psig.

6 Claims, 1 Drawing Figure

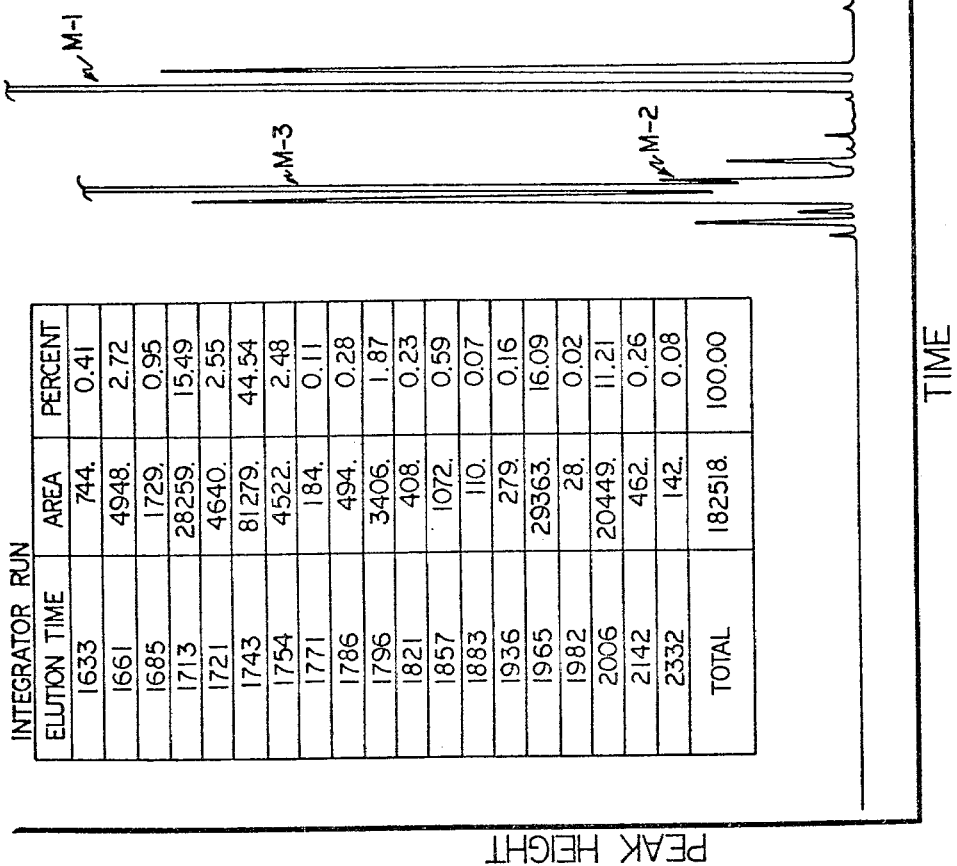

SELECTIVE CONVERSION OF D-ISOLIMONENE TO D-3-MENTHENE

The instant case is a continuation-in-part of application Ser. No. 005,138 filed Jan. 22, 1979 (now U.S. Pat. No. 4,204,080) incorporated herein by reference.

BACKGROUND OF THE INVENTION

The parent case Ser. No. 005,138 related to the preparation of 3-menthene and more particularly to a novel selective hydrogenation process utilizing a homogeneous ruthenium catalyst complex therefor.

It has now been found that d-3-menthene of high optical purity can be produced by the selective hydrogenation of d-isolimonene in the presence of minor amounts of a palladium hydrogenation catalyst at temperatures up to about 200° C. and pressures of preferably about 100–500 psig. Such selective hydrogenation process for the production of d-3-menthene of high optical purity is surprising in view of U.S. Pat. No. 3,407,241 (Booth) which teaches the selective conversion of d-trans-isolimonene predominantly to d-trans-2-menthene in 78 percent conversion with the production of no 8-menthene.

BRIEF SUMMARY OF THE INVENTION

It is well known that 3-menthene is a valuable intermediate in the synthesis of menthol. In the parent case, Ser. No. 005,138 it was shown that certain ruthenium catalysts were valuable in preparing 3-menthene from isolimonene.

The present invention is a process for catalytically hydrogenating optically active d-isolimonene in the presence of minor amounts of palladium catalysts at temperatures up to 200° C. and pressures of preferably about 100–500 psig to produce d-3-menthene of high optical purity. The hydrogenation can be conducted neat or by using an organic solvent.

DETAILED DESCRIPTION OF THE INVENTION

The hydrogenation catalysts useful in the present invention are palladium catalysts which are commercially available or may be prepared in situ prior to the hydrogenation conversion. Palladium catalysts on carrier supports, including carbon, calcium carbonate, barium sulfate and other common supports are preferred. Palladium on alumina base is especially preferred. Loadings of catalyst (percent metal on support) should be less than 5 percent preferably no higher than 2 percent. Preferred loadings are in the range of about 0.005 to 0.5 percent.

In addition to catalyst loading, the other critical parameters in the production of optically active d-3-menthene include the catalyst level, the hydrogen pressure and the reaction temperature. The catalyst level is defined as weight percent metal basis weight of d-trans-isolimonene to be converted to d-trans-3-menthene. Preferably levels are in the range of 0.001 to 0.5 percent with ranges less than 0.005 percent preferred. Temperatures up to 200° C. and operating hydrogen pressures in the range of 100–300 psig are preferred. Combinations of these operating parameters will result in the selective conversion of d-isolimonene to d-3-menthene in yields of about 40–80 percent with optical purity retention of at least 48 percent. Only a minor amount of 2-menthene will be present, usually less than five weight percent basis total product.

At the completion of the selective hydrogenation process, the d-3-menthene of high optical purity will be isolated from the reaction mixture by common techniques known to the art, including fractional distillation at from about 1 to about 300 millimeters of mercury. Catalyst components will preferably be reused for multiple conversions and replaced or supplemented only as needed.

Confirmation of the optical activity of the resulting d-3-menthene was established by conversion by epoxidation to cis and trans-3-menthene oxides, isomerization and purification to menthone and conversion to menthone enol acetate. Conversions of optical purity retention of at least 48 percent were demonstrated in this fashion.

For present purposes, the present invention is judged to be selective in the formation of product 3-menthene when a preponderance of 3-menthene over all other para-menthenes (chiefly 1-menthene usually) is contained in the product reaction mixture. Typically, the reaction mixture will contain about 40% to 70% by weight or more of the desired 3-menthene at the conclusion of the present process. Also, a valuable feature of the present process is the production of optically active 3-menthene from optically active iso-limonene.

The following examples show in detail how the present invention can be practiced but should not be construed as limiting. In this application, all percentages and proportions are by weight and all units are in the metric system, unless otherwise expressly indicated.

EXAMPLE 1

Isomerization of d-Isolimonene to d-3-Menthene

To a 2 l. monel Parr bomb was charged 432.0 g. of 92.4% pure d-isolimonene and 0.399 g. of 0.5% palladium on alumina catalyst (0.1 percent based on isolimonene). After purging three times with hydrogen, the system was pressured to 180 psig with hydrogen, heated to 120° C., and stirred for 14 hours at 120° C. while taking periodic samples. The reaction mixture was cooled and an additional 0.2 g. catalyst added. Agitation was continued at 120° C. under pressure for 18 hours. After cooling, the reaction mixture was filtered to yield 411.7 g. product containing 44.5 percent 3-menthene. Vapor pressure chromatography gave the analysis shown in Table 1.

The analyses were performed on a Perkin Elmer 900 instrument equipped with a 60 meter SP-2100 column programmed at 2°/min. starting at 75°. The individual peaks in the chromatogram were identified by retention time comparisons with authentic samples. VPC spectra of the 26 hour sample is shown as the FIGURE. 2-menthene (2.48 percent) appears as a distinct peak immediately following the 3-menthene component.

TABLE 1

| Sample Time | % Menthanes/ caranes | % Isolimonene | % 3-Menthene | % 1-Menthene | % Limonene | % 4(8)-Menthene | % 3,8(9)-Menthadiene | % Terpenolene 2,4(8)-Menthene |
|---|---|---|---|---|---|---|---|---|
| 0 | 4.64 | 92.36 | 1.57 | — | — | — | — | — |
| 4 | 23.95 | 26.55 | 33.59 | 2.66 | 2.45 | 6.40 | — | .34 |

TABLE 1-continued

| Sample Time | % Menthanes/ caranes | % Isolimonene | % 3-Menthene | % 1-Menthene | % Limonene | % 4(8)-Menthene | % 3,8(9)-Menthadiene | % Terpenolene 2,4(8)-Menthene |
|---|---|---|---|---|---|---|---|---|
| 10 | ? | 20.98 | 41.62 | 8.55 | 1.65 | 12.32 | .37 | 1.01 |
| 14 | 8.95 | 16.39 | 41.78 | 10.84 | 0.87 | 13.38 | .39 | .97 |
| 18 | 14.93 | 7.04 | 43.11 | 14.28 | .26 | 13.05 | .38 | .40 |
| 26 | 18.21 | 2.55 | 44.54 | 16.09 | .02 | 11.21 | .26 | .08 |

Fractional distillation of the final product provided 250 g. of material containing 64% d-3-menthene, or approximately 40% of theory based on d-isolimonene charged. This material was used in the following example.

EXAMPLE 2

Epoxidation of d-3-Menthene

To a mixture containing 245.0 g. of 64% d-3-menthene, 120.4 g. of sodium carbonate, and 568 ml of methylene chloride was added a solution containing 215.9 g. of 40% peracetic acid and 2.3 g. of sodium acetate. The addition was carried out at 10°–15° C. over a period of three hours after which the reaction mixture was allowed to come to room temperature over a 1.5 hour period and then stirred at room temperature for another two hours. At this point, 1 l. of water was added and the organics were isolated by repeated extraction with methylene chloride. Removal of the solvent provided 266.3 g. of oil containing 60.3% cis- and trans-3-menthene oxides. Gas chromatographic analysis was carried out as before with identification by comparison with authentic samples. Distillation of the product provided cis- and trans-3-menthene oxide [bp 68° (10 mm)] of 95.9% purity with an observed rotation of +23.3° (neat). This material was used in the following example.

EXAMPLE 3

Isomerization of cis- and trans-3-Menthene Oxide

A solution containing 0.45 g. of 70% perchloric acid in 238 g. of toluene was stirred at 20° and to it was added 119 g. of 95.9% cis- and trans-3-menthene oxide over a 45 min. period. Stirring was continued for 2.5 hr. after which the reaction mixture was neutralized with sodium bicarbonate, washed with saturated sodium chloride solution, and dried. Distillation provided 107.6 g. of material containing 93.1% menthone and iso-menthone. Re-distillation gave a fraction bp 78°–81° (10 mm) containing >99% menthones. The nmr spectrum of this product was identical to that of commercial material. The optical activity was obtained as shown in the following example.

EXAMPLE 4

Preparation of Menthone Enol Acetate

Acetic anhydride (57.6 g.) and 100% phosphoric acid (24.0 g.) were placed in a round bottom flask and stirred at room temperature under nitrogen. To this mixture, the menthone mixture (24.0 g.) obtained previously was added dropwise over a 20 min. period. After completion of addition, stirring was continued for 1 hr. at 45°. At this point, the material was poured onto 500 g. of ice and the organic matter was isolated by extraction with ether. Removal of solvent provided 38.2 g. of product containing 85% menthone enol acetate. Distillation provided pure (99.7%) material bp 36°–39° (1 mm) with an observed rotation of +33.9° (neat). Comparison with the reported rotation of +69.0° [Agr. Biol. Chem. 27, 433 (1963)] allows one to calculate an optical purity (ee) of 49% for the enol acetate. Thus, the d-3-menthene obtained by hydrogenation of d-iso-limonene (Example 12) is shown to have an optical purity (ee) of at least 49%.

What is claimed is:

1. A method of selectively producing d-3-menthene which comprises contacting d-isolimonene with hydrogen and a palladium hydrogenation catalyst under pressure and temperature conditions sufficient to produce optically active d-3-menthene as the major product component.

2. The method of claim 1 wherein the catalyst comprises palladium metal on a carrier support.

3. A method according of claim 1 wherein the catalyst is palladium on alumina.

4. A method according to claim 3 wherein the catalyst contains from about 0.01 to 4.5 percent palladium basis total weight of catalyst.

5. A method according to claim 4 wherein said catalyst is used in an amount from about 0.005 to 2.0 weight percent basis weight of d-isolimonene and the contacting is conducted at a hydrogen pressure of about 50–300 psig and a temperature up to about 200° C.

6. A method according to claim 5 wherein the hydrogen pressure is at least about 100 psig and the optical purity of the d-3-menthene is at least 48 percent.

* * * * *